United States Patent [19]

Kleipool

[11] 4,230,734

[45] Oct. 28, 1980

[54] FLAVORING WITH 4-METHYL-4-FURFURYLTHIO-PENTA-NONE-2

[75] Inventor: Reinerus J. C. Kleipool, Amersfoort, Netherlands

[73] Assignee: Naarden International, N.V., Naarden-Bussum, Netherlands

[21] Appl. No.: 967,596

[22] Filed: Dec. 8, 1978

Related U.S. Application Data

[63] Continuation of Ser. No. 776,763, Mar. 11, 1977, abandoned.

[30] Foreign Application Priority Data

Mar. 15, 1976 [NL] Netherlands .......................... 7602689

[51] Int. Cl.$^2$ ............................................. A23L 1/231
[52] U.S. Cl. .................... 426/535; 260/347.2
[58] Field of Search ...................... 426/535; 260/347.2

[56] References Cited

U.S. PATENT DOCUMENTS

3,702,253  11/1972  Winter et al. .......................... 426/535

*Primary Examiner*—Joseph M. Golian
*Attorney, Agent, or Firm*—Brumbaugh, Graves, Donohue & Raymond

[57] ABSTRACT

The invention relates to a process for changing, intensifying or supplementing the taste and/or flavor of foodstuffs and a new thiopentanone derivative useful as a flavor additive.

3 Claims, No Drawings

FLAVORING WITH 4-METHYL-4-FURFURYLTHIO-PENTANONE-2

This is a continuation of application Ser. No. 776,763 filed Mar. 11, 1977, and now abandoned.

In the food industry there is a constant demand for additives capable of imparting, supplementing or improving desired organoleptic properties in food products. Given the increasing demand for food products, the food industry has been compelled to use more and more raw products that fail to meet desired organoleptic requirements. Moreover, since the raw materials for most food products are generally of a natural origin their quality is often less than uniform. However, the addition of flavoring agents has made it possible to improve and to standardize the organoleptic quality of most food products. In particular the increasing use of proteins, other than of animal origin, has caused a corresponding demand for flavoring agents which are capable of imparting to these (non-animal) proteins a meat taste. Where non-animal and animal proteins are combined, the flavoring agents are used to amplify the meat taste of the animal protein sources.

The present invention relates specifically to the compound 4-methyl-4-furfurylthio-pentanone-2, having the formula

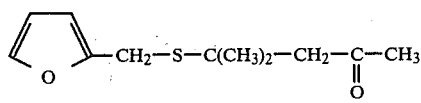
(I)

and to foodstuffs and flavoring compositions which contain an acceptable amount of compound (I). As used in this context, foodstuffs include foods, stimulants, drinks, medicines, etc. for human or animal consumption.

In Dutch patent application No. 73,10627, which has been laid open for public inspection, certain 4-alkylthiopentanones having the formula

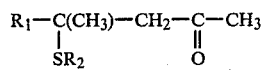

wherein $R_1$ is hydrogen or methyl ($Ch_3$) and $R_2$ is an alkyl radical have been disclosed as flavoring additives for citrus fruit products and other tropical fruit products.

Moreover, in the Dutch patent application No. 66,05854, which also has been laid open for public inspection, furfurylthio acetone having the formula

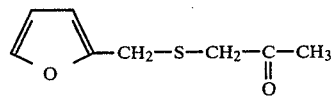

is disclosed as a compound, having a flavor, suggestive of roasted coffee.

It has now been found that the novel compound of the present invention, 4-methyl-4-furfuryl-thiopentanone-2, is a significant flavoring with a very strong flavor. In relatively low concentrations (up to about 0.5 ppm) the flavor strongly resembles roasted meat. In higher concentrations (above 0.5ppm), a grilled or burned-meat flavor is achieved, which also is vaguely suggestive of the flavor of black berries (ribes nigrum).

The compound of the present invention can be used for foodstuffs, in which a flavor needs to be imparted or intensified. Examples are: meat, particularly roasted meat, meat spices, soups, sauces, fish, cocoa coffee, nuts and other foodstuffs in which the above are ingredients or which must have these specific flavors.

The amount of the compound of the present invention, which is added to a certain foodstuff, largely depends on the particular foodstuff and on the effect to be obtained. Generally a concentration of 0.005 ppm of the novel compound in the foodstuff will yield a perceptible effect on the flavor. On the other hand, where concentrations exceed 1000 ppm the effect will be too strong and an unpleasant effect will prevail. Concentrations of the novel compound which range from between 0.02 and 100 parts per million (ppm) in foodstuffs generally yield a pleasant flavor effect; however, the best results are achieved when the concentration range is between 0.05 and 10 ppm.

The compound of the present invention can be added as such to a foodstuff or it can be incorporated into a flavor preparation together with usual flavor substances and flavoring agents. The compound or the flavor preparation, of which it is a part, can be diluted, if desired, with solid or liquid carriers, known in the food industry.

The novel 4-methyl-4-furfurylthio-pentanone-2 compound can be prepared according to known methods, e.g. by the addition of furfurylmercaptan to mesityloxide, the reaction scheme of which is set forth below:

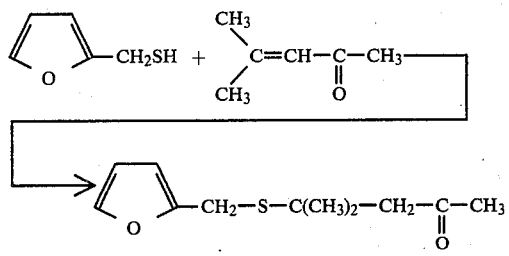

The following examples are provided as illustration of the preparation and application of the novel compound according to the present invention.

EXAMPLE I

Preparation of 4-methyl-4-furfurylthio-pentanone-2

57 g furfuryl mercaptan (0.50 mol) were added dropwise to a rigorously stirred solution of 54 g (0.55 mol) mesityl oxide and 0.5 g triethylamine in ether. The temperature was maintained at about 10° C. After all had been added the reaction mixture was heated for one hour under reflux. The reaction mixture was thereupon cooled and washed twice with 5 percent sulphuric acid solution and, thereafter with water to neutral reaction. The solution in ether was dried on $MgSO_4$ and evaporated. The residue was fractioned under reduced pressure. Yield 60%; boiling point 86° C./0.3 mm mercury.

EXAMPLE II

A flavor of grilled chicken was prepared according to the following recipe.

| | |
|---|---|
| 4-methyl-4-furfurylthio-pentanone-2 | 0.4 g |
| hexanal | 0.2 g |

| | -continued | |
|---|---|---|
| | 2,4-decadienal | 0.5 g |
| | alcohol 96% to | 998.9 g |
| | | up to 1000.0 g |

A chicken ragout was prepared of: 200 g margarine, 200 g flour, salt and 2 liter chicken broth made from 500 g chicken meat. To 1 liter of this ragout 0.5 g of the above mentioned flavor solution was added. This flavored ragout was compared by a panel of 7 persons with the unflavored ragout. It was unanimously agreed that the flavored ragout possessed a more intensive flavor of chicken meat, specially grilled chicken meat and was consequently more tasty than the unflavored ragout.

A chicken ragout was also prepared by replacing in the above recipe one half of the chicken broth by water and by adding per liter of ragout, 1g of the flavor solution. This ragout too was unanimously preferred to the unflavored ragout prepared exclusively with chicken broth. The flavored ragout prepared with chicken broth and water was considered to be equal to the flavored ragout already mentioned prepared exclusively with chicken broth.

EXAMPLE III

A flavor of grilled beef was prepared according to the following recipes:

| A | 4-methyl-4-furfurulthio-pentanone-2 | 0.4 g |
|---|---|---|
| | hexanal | 0.2 g |
| | maltol | 0.05 g |
| | 3-methyl-2-hydroxycyclopentene-2-on | 0.05 g |
| | 2,4-decadienal | 0.2 g |
| | alcohol 96% | 999.10 g |
| | | 1000.00 g |
| B | hexanal | 0.4 g |
| | maltol | 0.1 g |
| | 3-methyl-2-hydroxycyclopentene-2-on | 0.1 g |
| | 2,4-decadienal | 0.4 g |

| | -continued | |
|---|---|---|
| | alcohol 96% | 999.0 g |
| | | 1000.00 g |

1500 g minced meat were mixed with 2 eggs, 20 g breadcrumbs and peper and salt. To 500 g of this minced meat, 0.3 g of flavor solution A was added. A second, 500 g portion of the minced meat was flavored with 0.3 g of flavor solution B. The three portions of 500 g minced meat balls formed, were subsequently grilled in margarine. The three portions of minced meat were subsequently judged by a panel of 7 persons. The minced meat flavored with flavor B was estimated somewhat higher on the average than the unflavored minced meat. It was, however, unanimously judged that the minced meat flavored with flavor mixture A possessed a clearer and more tasty flavor of grilled beef than the two other kinds of minced meat. Moreover, the minced meat flavored with flavor mixture A gave as the only one a more tasty gravy clearly reminding of grilled meat.

I claim:

1. A process for amplifying or changing the flavor of a food product, comprising adding to the ingredients of said food product a thiopentanone compound of the formula

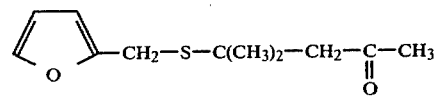

in an amount ranging between about 0.005 to about 100 ppm.

2. A process according to claim 1 wherein the concentration of the pentanone compound is between 0.05 and 10 parts per million.

3. Food products comprising, as a flavor additive, the compound 4-methyl-4-furfurylthio-pentanone-2 in an amount ranging between about 0.005 to about 100 ppm.

* * * * *